Feb. 10, 1976 R. H. McCOLLEY Plant Pat. 3,830
PHILODENDRON PLANT
Filed Nov. 1, 1974
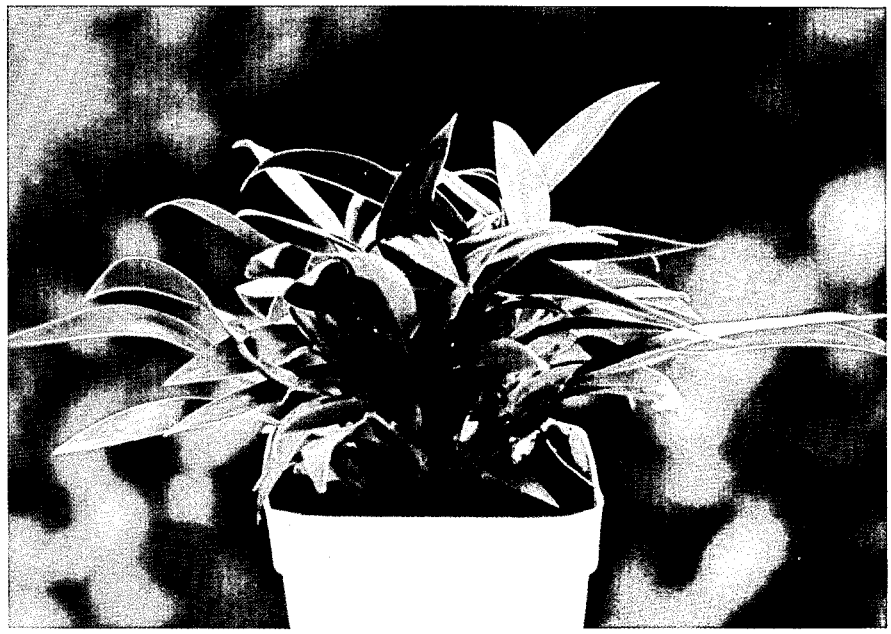

United States Patent

Plant Pat. 3,830
Patented Feb. 10, 1976

3,830

PHILODENDRON PLANT

Robert H. McColley, P.O. Box 17126, Orlando, Fla. 32810

Filed Nov. 1, 1974, Ser. No. 520,105
Int. Cl. A01h *5/00*
U.S. Cl. Plt.—88 1 Claim

ABSTRACT OF THE DISCLOSURE

There is disclosed a philodendron plant characterized by its resistance to wilting in low moisture and high temperature conditions form retention and slow growth indoors, thick, rubbery, generally extremely small lanceolate shaped leaves which are dark grayish green, and the petioles and stems dark red.

DESCRIPTION OF THE INVENTION

My present invention which I denominate Pincushion comprises a new and distinct variety of Philodendron plant, developed in my greenhouse by pollinating the standard plant with pollen from a seedling selected by me from the same seedling and self breeding. The standard plant referred to is from a seedling selected by me for a breeding program which I have carried on for many years, availing of the several Philoendron species *wendlan di, erubescens, imbe, hastatum* and an unidentified species.

The form of my present invention is new to Philodendrons since it is a miniature, self-branching form, propagated by division, never vining and surviving under the most adverse conditions. My new variety has been asexually reproduced by division, each division making a cluster, never vining, reproduction having been effected in the vicinity of Orlando, Fla., and been found to retain its distinctive characteristics through successive asexual reproduction.

Testing of this new variety has been undertaken under the most adverse conditions in California and Florida, and the variety has proven itself to be a superior, miniature foliage plant in each case.

My new variety is not similar to any Philodendron in cultivation nor to any described by Graf Bailey or Das Pflansenreich.

The visual features of my distinctive new variety which are recognizable, include the ovate leaf shape, miniature, self-branching form of growth.

The tip of each leaf is lanceolate and the venation is pinnate. The venation is smooth on the leaves and the surfaces are likewise.

The width of the average leaf is about 40% of the length. The plant form itself is extremely compact.

The leaves assume horizontal to semi-erect positions and the internodes are extremely close, with redwinged petioles.

Among other general characteristics of the plant which distinguish the same include the ability to withstand extremely low light intensity and low soil moisture content for weeks. High temperatures do not seriously affect the plant.

Leaves are rather thick, rubbery and withstand bruising and dehydration as suggested.

The plant is very resistant to bacterial soft rot and virtually immune to "shot gun" fungus.

Indoor growth is slow and the desired form is retained longer than varieties currently available.

The following detailed specifications are based on observations made in my greenhouse in Orlando, Fla. These specifications may be affected somewhat by varying environmental conditions, but where environmental conditions remain such as those present during development, including temperature, humidity and day length, the plants will reproduce and develop very uniformly.

The accompanying drawing, forming a part of the specification, shows a typical plant of my new variety. References are made to the Nickerson Color Fan published by Munsell Color Company, with observations being recorded by daylight illumination under vinyl of not more than 30% shade.

I. *Form Characteristics*

1. Leaf shape
   - (a) Mature—lanceolate
   - (b) Immature—lanceolate
   - (c) Tip—acuminate
   - (d) Base
     - (1) Mature-acute
     - (2) Immature—cordate
   - (e) Displacement—smooth
   - (f) Margin—entire
   - (g) Venation—smooth
2. Leaf attachment—stalked
3. Leaf arrangement—alternate, erect
4. Petiole—very short, winged, erect
5. Stem—short, heavy internodes ¼"
6. Overall appearance—dense, clustered

II. *Size Characteristics of Typical Commercial Size*

1. Leaf itself
   - (a) Width (widest point—1"
   - (b) Width (1" from tip)—⅝"
   - (c) Length—2½"
2. Petiole
   - (a) Length—1½"
   - (b) Diameter (center)—⅜"–½"
   - (c) Internode spacing—¼"
   - (d) Stem diameter—⅜"

III. *Color Characteristics*

1. Leaf (top 6 to 7 leaves)
   - (a) Top—10GY 3/2
   - (b) Bottom—darker—2.5R 4/10
   - (c) Margin—2.5R 3/7
2. Leaf (old bottom leaves)
   - (a) Top—lighter—7.5GY 4/4
   - (b) Bottom—7GY 6/8
3. Leaf venation
   - (a) Midrib—5R 3/7
4. Stem—2.5R 3/7
5. Petiole—5R 3/7

I claim:

1. A new and distinct variety of Philodendron plant, substantially as herein described, characterized as to novelty by its ability to withstand low moisture and high temperature conditions, its slow growth and miniature, dwarf form retention indoors during propagation and growth, its thick, rubbery, small lanceolate shaped leaves of dark grayish green color, with dark red petioles and stems.

No references cited.

ROBERT E. BAGWILL, Primary Examiner